United States Patent
Devereux

(10) Patent No.: US 10,474,771 B2
(45) Date of Patent: Nov. 12, 2019

(54) CALCULATION ORDER MANAGEMENT FOR A SEQUENTIAL-MODULAR PROCESS SIMULATOR

(71) Applicant: HONEYWELL INTERNATIONAL INC., Morris Plains, NJ (US)

(72) Inventor: Brian M. Devereux, Elk Grove Village, IL (US)

(73) Assignee: Honeywell International Inc., Morris Plains, NJ (US)

(*) Notice: Subject to any disclaimer, the term of this patent is extended or adjusted under 35 U.S.C. 154(b) by 193 days.

(21) Appl. No.: 15/626,998

(22) Filed: Jun. 19, 2017

(65) Prior Publication Data
US 2018/0365353 A1    Dec. 20, 2018

(51) Int. Cl.
G06F 7/00    (2006.01)
G06F 17/50    (2006.01)

(52) U.S. Cl.
CPC ............... *G06F 17/5009* (2013.01)

(58) Field of Classification Search
CPC .................................. G06F 17/5009
See application file for complete search history.

(56) References Cited

U.S. PATENT DOCUMENTS

| | | | |
|---|---|---|---|
| 7,614,037 B2 | 11/2009 | Gavrilov | |
| 7,908,022 B2 | 3/2011 | Franco | |
| 8,978,010 B1 | 3/2015 | Thumfart et al. | |
| 2009/0182176 A1* | 7/2009 | Griffin | C01B 3/24 568/700 |
| 2012/0156741 A1* | 6/2012 | Chheda | C12P 7/10 435/155 |
| 2013/0127891 A1 | 5/2013 | Kim et al. | |
| 2016/0004803 A1 | 1/2016 | Chyou | |
| 2016/0124739 A1* | 5/2016 | Zongker | G06F 16/9024 717/172 |
| 2019/0217283 A1* | 7/2019 | Glover | B01D 3/009 |

OTHER PUBLICATIONS

Bernhard Haeupler et al "Incremental Cycle Detection, Topological Ordering, and Strong Component Maintenance",ACM Transactions on Algorithms, vol. 8, No. 1, Article 3, Publication date: Jan. 2012, p. 1-33 (Year: 2012).*

* cited by examiner

*Primary Examiner* — Timothy A Mudrick
*Assistant Examiner* — Abdou K Seye

(57) ABSTRACT

A method of chemical process simulation includes providing a Sequential-Modular process simulator having a simulation algorithm. Responsive to receiving a process flowsheet creating a directed graph (DG) which represents a topology of the process flowsheet with components interconnected as nodes and process streams including recycle streams represented as cycles, with dependencies between process streams adding cycles. Partitioning the components into a first portion including strongly-connected component groups (SCCGs) along with individual components. An initial location is provided for each cycles for the SCCGs to generate a directed acyclic graph (DAG). An initial calculation order is determined for the flowsheet from the DAG, including an order for calculation within the SCCGs themselves. The SCCGs and components as nodes and process streams as edges with a graphical indication representing each cycle for the SCCGs along with the initial calculation order are graphically displayed, wherein the initial calculation order is user modifiable.

15 Claims, 6 Drawing Sheets

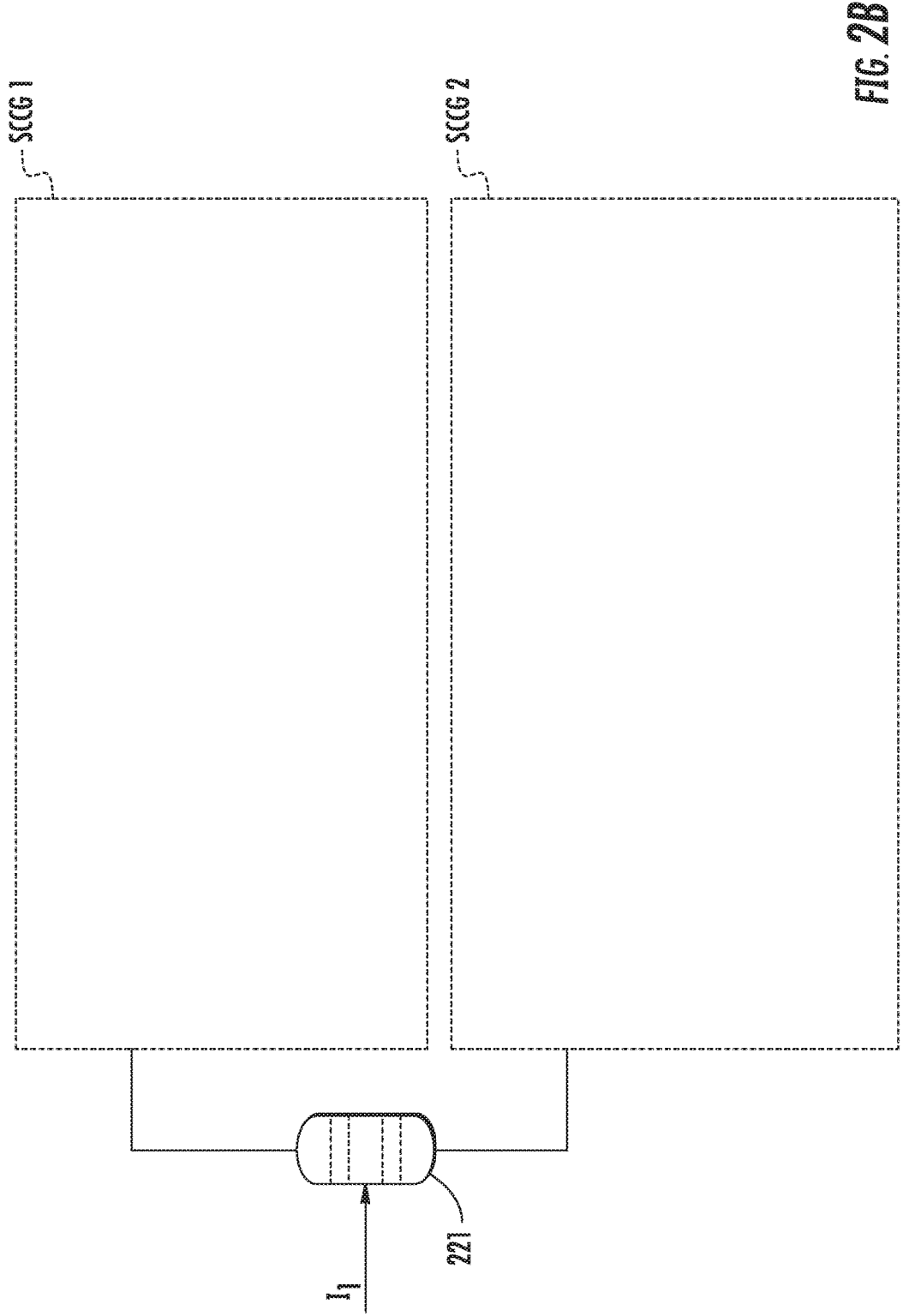

CALCULATION ORDER MANAGEMENT FOR A SEQUENTIAL-MODULAR PROCESS SIMULATOR

FIELD

Disclosed embodiments relate to chemical process simulators.

BACKGROUND

Chemical process facilities can include manufacturing plants, chemical plants, crude oil refineries, ore processing plants, and paper or pulp manufacturing plants. These process facilities typically use continuous processes and fluid processing. Process simulation tools have been used to model the behavior of industrial and chemical processes. The simulation tools can reduce the efforts needed to develop representative process models that predict the performance of a process.

Process flowsheets (also known as process flow diagrams) are widely used in chemical engineering and process engineering to represent chemical process components (equipment) and chemical flows among chemical process components, and to determine chemical process parameters through simulation. Chemical process simulators model the behavior of chemical processes such as those run in a chemical process facility, including solving a flowsheet that is also known as a process flow diagram (i.e., convert from a process flowsheet to a simulation flowsheet, i.e., replace the process units with appropriate simulation units) to perform steady-state heat and mass balances, sizing, and costing calculation for a chemical process.

Current process simulators typically use one of two classes of techniques to solve the process flowsheet, either the sequential-modular (SM) or simultaneous (equation-oriented (EO)) calculation methods. The SM method is the primary approach used by commercial process simulators because it is generally more robust than the EO method which requires that one already has a good initial guess for the solution of the large system of equations representing the process flowsheet. This is rarely true a priori and typically a few iterations of the SM method are used to initialize the EO method. The advantages of the EO method include being potentially much faster than the SM method and also providing more flexibility in specifying the dependent variables and independent variables of the flowsheet.

The topology of a process flowsheet can be represented as a directed graph (DG or 'flowsheet digraph') with the chemical process unit operations, performed by equipment such as mixers and reactors as the vertices of the DG and the process streams as the edges of the DG. A single unit operation or set of unit operations is referred to herein as 'components' that have attached process streams. The process flowsheet is thus represented by the simulator by components that are interconnected by connections (shown as lines in the process flow diagram) for the process streams representing a chemical flow in some direction. Some of the process streams may form a recycle loop. A recycle loop is a term denoting a sequence of process streams which returns material or enthalpy (heat) from a downstream component back to an upstream component. The presence of any recycle loop(s) in the flowsheet makes the resulting DG have a cycle(s), and is thus not acyclic.

For SM simulators each component class (such as mixers, reactors, or distillation columns) has a built-in calculation procedure with specified input and output variables. The simulator will first determine an order to calculate the components. It will then attempt to calculate all the components (and attached streams) in order. A calculation is possible if all the input variables for the component calculations are known. After attempting the calculation of all components, the process is repeated until no more calculations can be made. If there are recycle loops present in the flowsheet and thus cycles in the DG one needs to assume an initial 'guess' for one the process streams in the loop (usually referred to as the "tear" stream) and iterate this procedure until convergence is achieved. Examples of commercially available SM process simulators include ASPEN and CHEMCAD.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments recognize commercially available SM process simulators offer limited functionality for the user to view and modify the calculation sequencing (order) of the unit operations performed by the components and recycle convergence specification for chemical simulation cases. As noted above, the topology of a process flowsheet is typically represented as a DG with the components providing the chemical process unit operations as vertices and process streams as edges of the flowsheet. The presence of recycle loops in the flowsheet result in cycles in the DG. The DG can be augmented with additional calculation dependencies between the process streams. For example, there might be a temperature specification of a particular process stream that needs to be met by adjusting the pressure of a different upstream process stream. In general these dependencies will introduce additional cycles in the DG. Dependencies such as recycle streams thus introduce additional cycles in the DG.

The following acronyms are used herein with definitions provided below:

Component=equipment (e.g., drums, mixers) that has associated process piping and valves that performs a single unit operation which corresponds to a node providing unit operations in the process flowsheet.

DG=directed graph which is a set of vertices and edges with direction (shown with arrows) that is a mathematical object representing the connectivity between the components in a process flowsheet. The DG has strongly-connected components (SCCs) which may or may not have cycles that correspond to recycle streams in the process flowsheet. If a DG has no cycles it is referred to as a directed acyclic graph (DAG). A DG can always be decomposed into a DAG with vertices that are either single components or groups of strongly-connected components (SCCGs). Each SCCG will always contain one of more cycles. If the original DG does not contain cycles (i.e. it is already a DAG), the decomposition of the DG into SCCs will result in a DAG which is identical to the original DG.

SCCs of a DG is a subgraph that is strongly-connected, and is maximal with the property where no additional edges or vertices from the DG can be included in the subgraph without breaking its property of being strongly-connected. The collection of SCCs forms a partition of the set of vertices of the DG.

SCCG=SCC group, which is a group of SCCs with at least one cycle within.

DAG=directed acyclic graph with no cycles that is generated from decomposition of the DG that contracts each SCCG into a single vertex. When the DG is reduced to a DAG (no cycles) the nodes of the DAG become either components (providing single unit operation) or SCCGs (providing multiple unit operations). A DAG can always be generated from decomposition of a DG that contracts each SCCG into a single vertex; when the DG is reduced to a DAG (no cycles) the nodes of the DAG become either components (providing single unit operation) or SCCGs.

PFD view=process flow diagram view of the DAG for the user, where the nodes in this view represent single components or groups of components (SCCGs). There can be many different PFD views provided for a flowsheet. One particular view important herein is a PFD view of the flowsheet DAG resulting from the decomposition of the full flowsheet into SCCs.

As noted above a "recycle stream" in the flowsheet results in a "cycle" in the DG representation. A user of the simulator will not refer to graphs or cycles as recycle streams and cycles as they are abstract mathematical ideas used in the underlying computer algorithms disclosed simulators use for its calculations.

The above-described problems are solved by disclosed embodiments through partitioning the DG into a DAG of single components and SCCGs with removal of any cycles between the SCCs. The SCCs in this situation are thus either individual components performing individual unit operations or groups of components (thus SCCGs) performing groups of unit operations and attached streams. All loops will exist only within a SCCG. The simulator should provide the user an option of graphically displaying the flowsheet represented as mixed set of components and SCCGs along with a user-modifiable calculation order for these SCCs.

For each SCCG that contains more than a single component (and thus contains one or more cycles), the simulator can graphically display the partial flowsheet representing that component. This view will also present a user-modifiable calculation order for the unit operations within the SCCGs, as well as user-modifiable specifications related to the loops present within the SCCGs.

BRIEF DESCRIPTION OF THE DRAWINGS

FIG. 2B shows a DAG formed by removing the contents of the boxes labeled SCCG1 precursor and SCCG2 precursor in FIG. 2A. The resulting SCCG1 and SCCG2 boxes have a single inlet stream and two outlets streams as in FIG. 2A.

DETAILED DESCRIPTION

Figure 1:
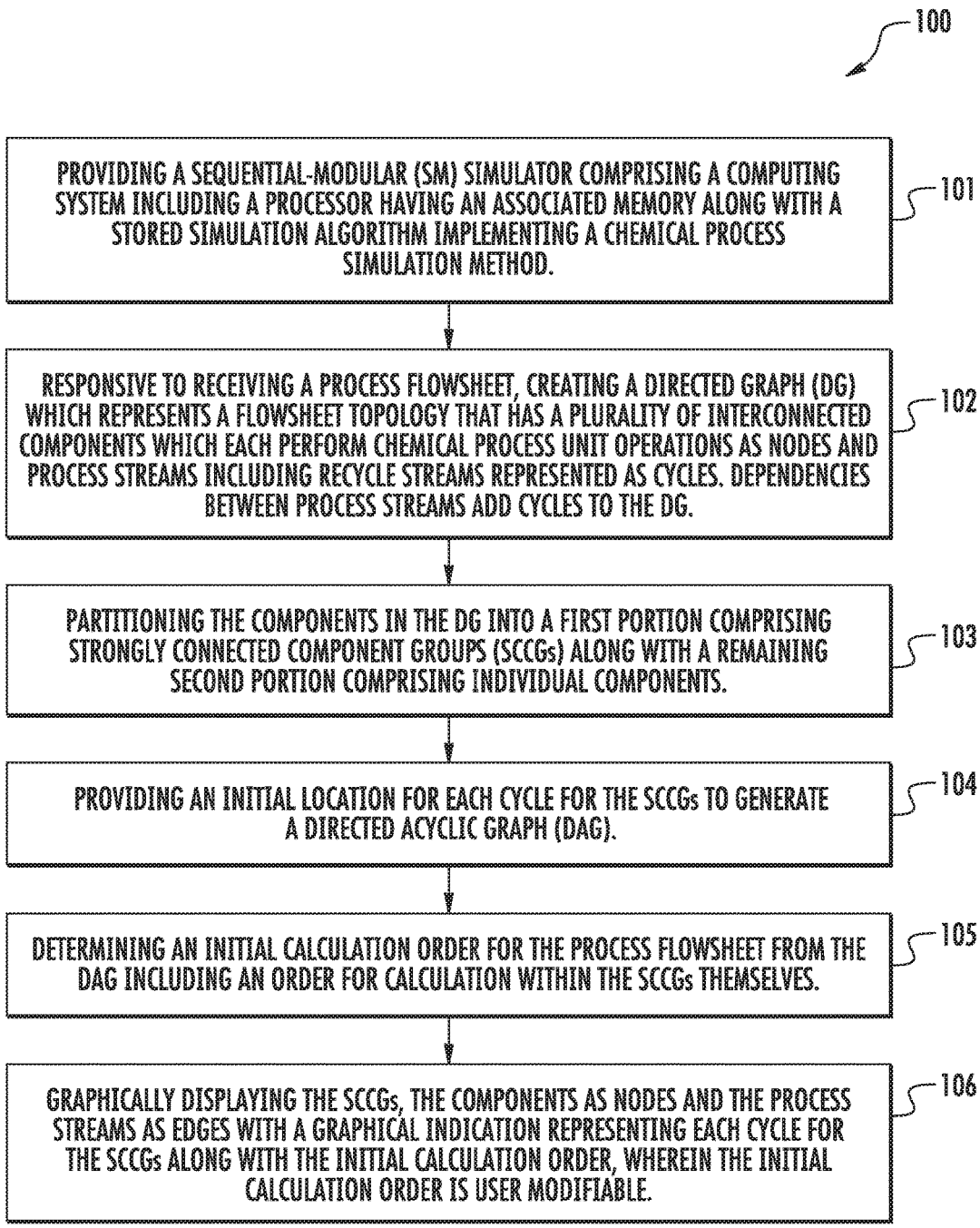
FIG. 1 is a flow chart showing steps for an example method of chemical process simulating for a sequential-modular process simulator including calculation order management, according to an example embodiment.

Disclosed embodiments are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring certain aspects. This Disclosure is not limited by the illustrated ordering of acts or events, as some acts may occur in different orders and/or concurrently with other acts or events. Furthermore, not all illustrated acts or events are required to implement a methodology in accordance with the embodiments disclosed herein.

FIG. 1 is a flow chart showing steps for an example method 100 of chemical process simulation, according to an example embodiment. Step 101 comprises providing a SM simulator comprising a computing system including a processor having an associated memory along with a stored simulation algorithm including calculation order management implementing the method 100. The calculation order management includes determining a default calculation order. Step 102 comprises responsive to receiving a process flowsheet from a user, creating a DG which represents a flowsheet topology that has a plurality of interconnected components which each perform chemical process unit operations as nodes and process streams including recycle streams represented as cycles. Dependencies between process streams add cycles to the DG. See FIG. 2A described below which shows no additional calculation dependencies in the view provided, only components performing the unit operations and the streams.

The classes of chemical unit operations include reactors, mixers, and distillation columns. The chemical material that flows between various unit operations is referred to as a "stream" where it is often actual material flowing through pipes. The cycles in the DG are usually process stream recycle loops, but a cycle can also represent an iterative calculation loop where some process variable specification is made downstream of a separate process variable upstream. For example, specifying a reactor conversion and calculating the required temperature of the feed stream to the reactor.

Step 103 comprises partitioning the components in the DG into a first portion comprising SCCGs along with a remaining second portion comprising individual components. The components will thus either be single operations or SCCCGs being sets of multiple operations connected by one or more cycles. Displaying the SCCs provides the simulation user insight into which groups of recycle streams are independent. The user can then make informed decisions on the recycle convergence specifications for that particular component. Without knowledge of the decomposition resulting from the partitioning, the user will not know how all the recycle streams are related, especially for larger flowsheets.

In one embodiment, for example, Tarjan's algorithm may be used to find the SCCs in the DG. Tarjan's algorithm may take a DG as input and may generate a partition of the graph's nodes into the graph's SCCs. Each node of the DG may appear in one and only one SCC, even if the node appears in a SCC by itself. Tarjan's algorithm may begin a depth-first search from the node that represents the final job that may be in the primary buffer. Subsequent depth-first searches may be conducted on any nodes that have not yet been found. In one embodiment, the search may not explore any node that has already been encountered. The SCCs may form the subtrees of the search tree, where the roots of the search tree may be the roots of the SCCs. Kosaraju's algorithm also known as the Kosaraju-Sharir algorithm may also be used for partitioning the DG into SCCs to generate a DAG showing interconnections between the SCCGs.

Figure 2A:
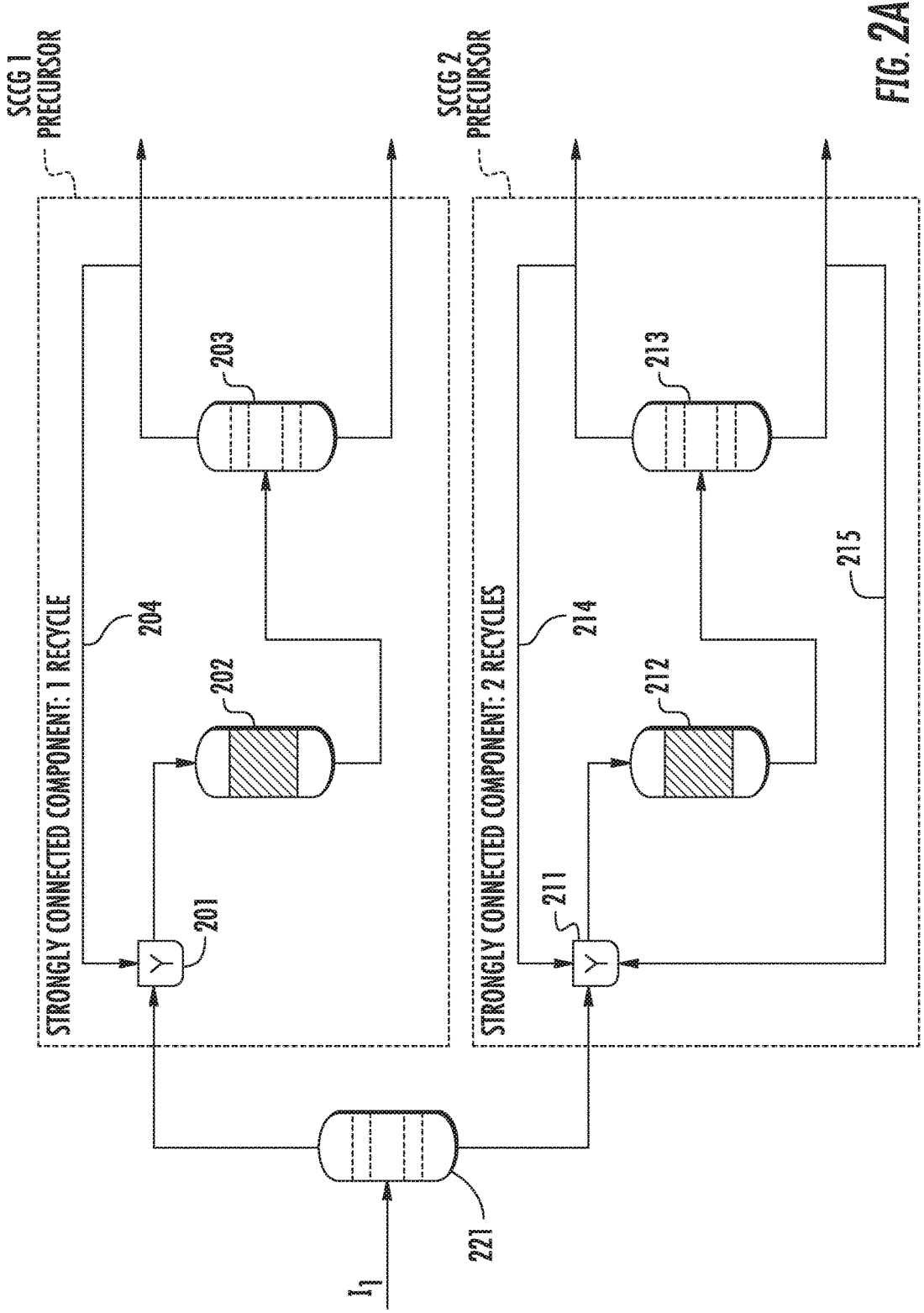
FIG. 2A shows an example partitioning/decomposition of a simplified DG into components and SCCG precursors shown as SCCG1 precursor and SCCG2 precursor showing interconnections between the SCCs.

Known chemical process simulators in contrast do not represent the management of calculation order and recycle calculation specifications organized by the SCC partitioning/decomposition of the DG. For example, in one known product the user can create inefficient flowsheets by decomposing the flowsheet into sub-flowsheets which are not strongly-connected components. It is recognized the recycle calculation will be inherently inefficient in this scenario and the user will typically be unaware of this problem choices for the recycle solution. There is no capability in this product to provide the user any guidance in creating flowsheet specifications that allow the efficient solution of recycles. See FIG. 2A showing a DG partitioned into SCCG precursors. The cycles only exist within the SCCGs, not between the components. As noted above, the components will either be single operations or sets of multiple operations connected by one or more cycles (thus be SCCGs).

Step 104 comprises providing an initial location for each cycle for the SCCGs to generate a DAG. The cycles can be determined directly from the DG by using a graph-traversal algorithm. It is generally up to the user to provide an initialization for a stream somewhere on the cycle. This stream is referred to as a "tear" stream, since a user tears the "recycle" apart at this location.

Step 105 comprises determining an initial calculation order for the process flowsheet from the DAG including an order for calculation within the SCCGs themselves. FIG. 2B shows a DAG derived from the representation in FIG. 2A, and FIG. 3 an initial calculation order for a DAG unrelated to the one shown in FIG. 2B. In order to modify the DG in FIG. 2A into a DAG, the simulation algorithm replaces the contents of the two sections within the boxes shown with small, single boxes labeled SCCG1 and SCCG2. These single empty boxes should each have a single inlet stream and two outlets streams as in the original FIG. 2A.

The initial calculation order is user modifiable. In general this initial calculation order is not unique, but will not affect the calculation speed of the simulation unless parallel processing algorithms are used, since each component is only calculated a single time. In the case where parallel processing capabilities are available, the user can be presented with a visual indication of what operations might form independent branching choices for parallel calculations and an opportunity to reorder the calculation order based on the parallel branching scheme selected. The user may then improve parallel processing solutions for a particular problem of interest by modifying the initial calculation order to suit the particular parallel processing scheme.

Step 106 comprises graphically displaying the SCCGs, the components as nodes and the process streams as edges with a graphical indication representing each cycle for the SCCGs along with the initial calculation order, wherein the initial calculation order is user modifiable. The user is presented with the calculation order management functionality as described above on a suitable display which allows users to make simulation changes to both the calculation order for the SCCs and optional calculation management within SCCGs with cycles including specifying new locations for the cycles. In addition the user is provided the ability to partition the set of cycles into sets of cycles that are solved by the simulator simultaneously.

Process simulators have wide applications in the areas of process design, process optimization, and process control. The simulations can be used to develop entirely new processes, optimize operating conditions for an existing design, or evaluate alternate process flow schemes. The results of the simulation may be compared against the real-time measurements of an operating plant and used to change process parameter setting(s) to modify the operating conditions to achieve a desired performance.

Modern simulators typically allow the user to created nested partitions of the flowsheet (sub-flowsheets) for reasons of visual or logical organization. In general this is completely unrelated to the disclosed partitioning of the DG into SCCs described above (which is not nested). Often the user desires to solve these sub-flowsheets independently of parent flowsheet. In this situation using known simulators the starting point of the calculation order management begins at the sub-flowsheet level, and a complete analysis is done and stored independently of the parent flowsheet results.

Figure 4:
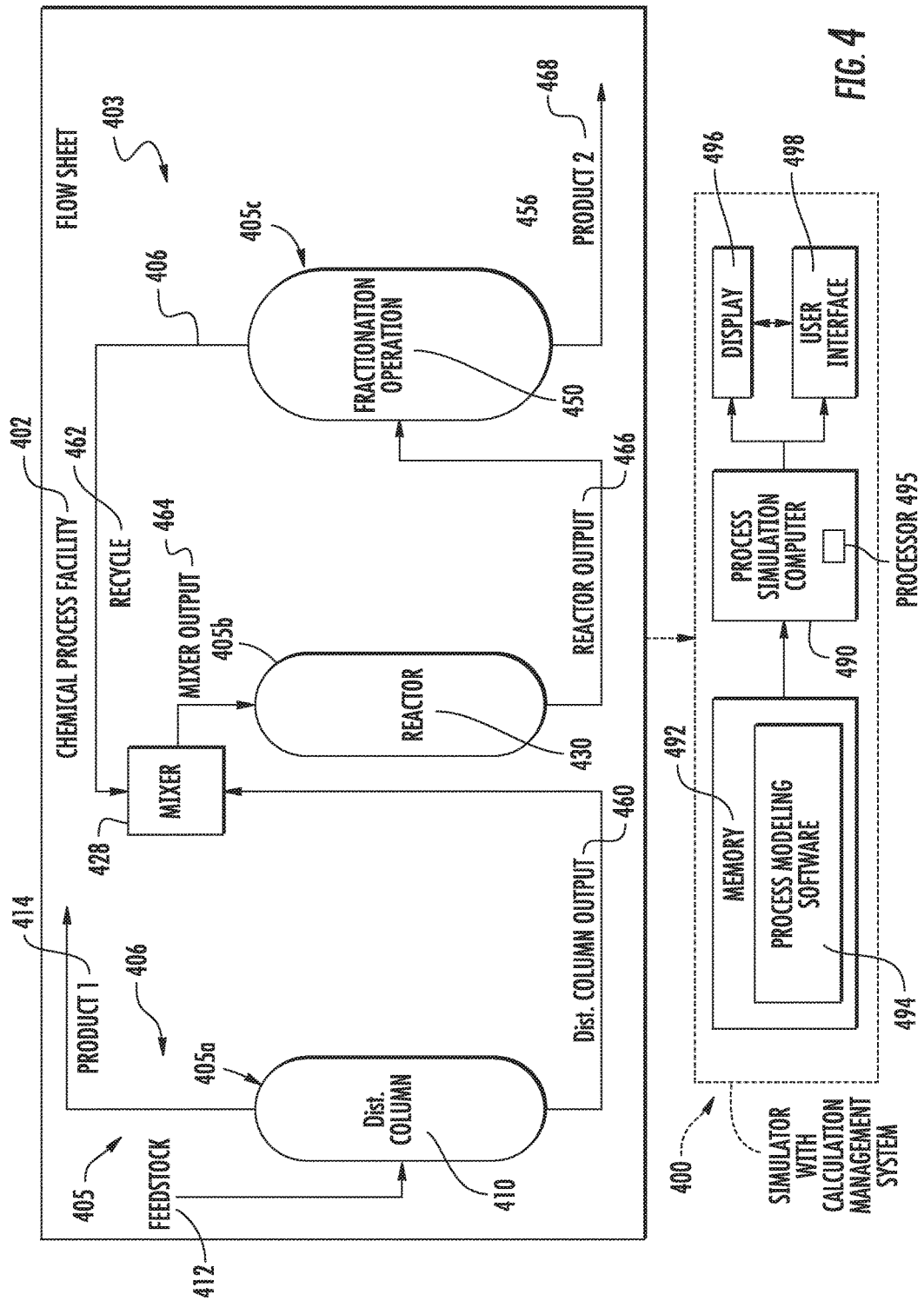
FIG. 4 is a block diagram of an example chemical process computer implementing a disclosed simulation system for a sequential-modular process simulator including calculation order management, according to an example embodiment.

In FIG. 4 described below the process simulation computer 490 including a processor 495 executing process modeling software 494 can interact with a user via a display 496 with a graphical user interface (GUI). In this situation the SCCGs contain one or more cycles. If the cycle is comprised of process streams, one of the process streams in the cycle should be selected as the stream to be initialized. This stream is known as the "tear" stream since it tears or breaks the cycle corresponding to the recycle loop in the flowsheet. Once the location of all "tear" streams are specified, the cycles in the DG are removed to provide a DAG and an initial (or default) calculation order can be determined by a topological sort of the DAG.

Modifications to this default calculation order can be made as described above. Any changes to the locations of the "tear" streams will generally involve a new determination of the calculation order. The simulator can provide facilities for recommending the locations of "tear" streams. The independent display of the flowsheets represented by the SCCs provides the user insight into which groups of recycle streams are independent. The user can then make informed decision on the recycle convergence specifications for that particular component group, such as partitioning the recycles into sets with different convergence algorithms and specifications.

FIG. 2A shows an example decomposition resulting from partitioning of a simplified example DG with each SCC uniquely labeled including identifying the SCCGs shown as SCCG1 precursor and SCCG2 precursor showing interconnections between the SCCs therein with cycles shown. The disclosed calculation management system/method can thus provide a PFD representation of the SCCs or other component each uniquely labeled. SCCG1 precursor is shown including SCCs 201, 202 and 203 with a cycle 204 between SCCs 203 and 201. "Cycles" in this context as noted above thus can represent physical stream recycles as well as abstract calculation recycles. As described above and known in the art, recycles are cycles/loops in the calculation sequence of the flowsheet where the output of one calculation is the input of another calculation earlier in the sequence. SCCG2 precursor is shown including SCCs 211, 212 and 213 with a cycle 214 between SCC 213 and SCC 211 and another cycle 215 between SCC 213 and SCC 211.

The SCCs in a DAG will either be a single operation or sets of multiple operations connected by one or more cycles where the cycles only exist within the SCCGs. Component 221 is shown in FIG. 2A receiving an input flow $I_1$ that provides a single operation and is thus not shown as being part of any SCCG precursor.

FIG. 2B shows a DAG formed by removing the contents of boxes labeled SCCG1 precursor and SCCG2 precursor in FIG. 2A. The resulting SCCG1 and SCCG2 boxes are shown having a single inlet stream and two outlets streams.

Figure 3:
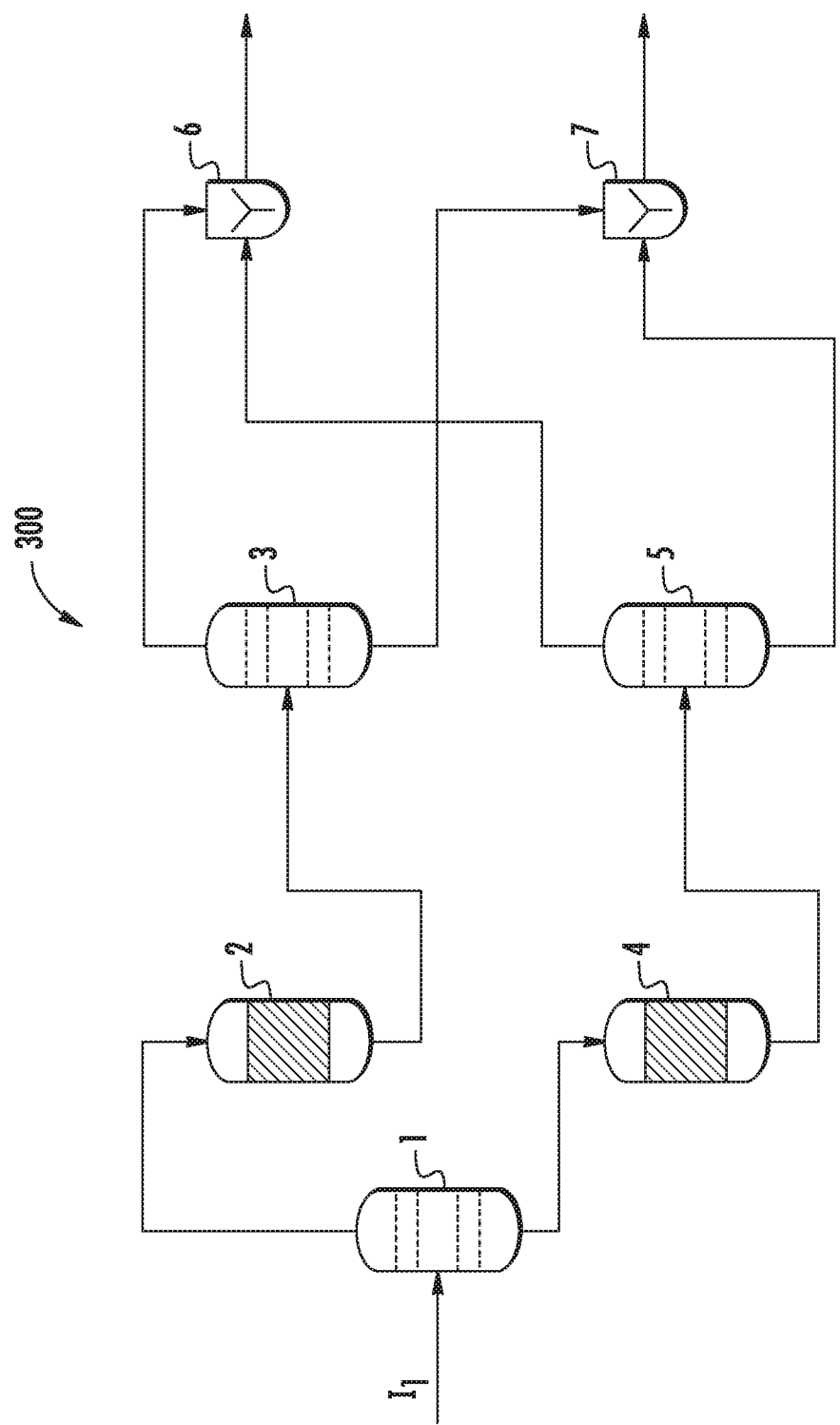
FIG. 3 shows a DAG resulting from an example topological sorting of a DG, where the number labels shown indicate the sorted order which is the calculation order for the flowsheet operations.

FIG. 3 shows a DAG 300 resulting from an example topological sorting of a DG, where the number labels shown indicate the sorted order which is the calculation order for the flowsheet operations. The DAG 300 has no relation to the DAG shown in FIG. 2B. The number labels (1 to 7) shown in FIG. 3 indicate the resulting sorted initial calculation order for the flowsheet operations with 1 (one) being the first operation to take place in the calculation order.

Regarding calculation management within SCCGs with cycles, any SCCG that contains multiple operations will contain cycles, either process streams or calculation-based cycles. The disclosed management system/method can provide the number of independent cycles within that SCCG and a list of suggested locations for the cycles (also known as tear streams). The user can accept the suggested locations or specify other locations for the cycles. In addition one can be able to partition the set of cycles into sets of cycles that are solved simultaneously. Once the location of the cycles is specified, a single iteration of the DG (with proper initialization of the cycles) represents a DAG (with torn edges/streams) and the calculation order can be determined by topological sorting.

FIG. 4 is a block diagram of an example SM process simulator with calculation management system 400 for simulating a chemical process run at a chemical process facility 402 with its simplified process flowsheet shown as 403, according to an example embodiment. Chemical process facility 402 can be any of a variety of different manufacturing or processing plants that handle, process, store and transport liquid or fluid chemicals and materials. Chemical process facility 402 can include manufacturing plants, chemical plants, crude oil refineries, ore processing plants, paper manufacturing plants and water processing plants. These industries and facilities typically use continuous processes and fluid processing.

Chemical process facility 402 includes various process elements or unit operations 405 including 405a, 405b and 405c that are inter-connected connected via pipes or conduits represented as various flow streams or fixed process stream connections 406. Chemical process facility 402 is represented by a flowsheet 403 having a flowsheet topology. As known in the art, the flowsheet topology defines a general flow of the chemical process including the components performing the unit operations connected by fixed process stream connections 406. In one embodiment, flowsheet 403 can include one or more nested sub-flowsheets. Nested sub-flowsheets are self-contained modules including one or more portions of the overall flowsheet 403.

Components can include a wide variety of chemical process units such as distillation columns, reactors, fractionation operations, heaters, holding tanks, valves, catalytic converters, mixers, separators, reactors, compressors, grinders, floatation tanks, pumps, expanders, distillation units, surge tanks, accumulators, relief valves, absorbers, filters, and heat exchangers. Each component performs a unit operation function involving one or more chemical ingredients or other products. For example, a chemical processing plant can include a distillation column that separates constituent chemical ingredients into individual components based on vapor condensing points to produce a desired chemical product. Chemical process facility 402 can produce several different types of chemical products. The production of each product can be performed by one or more of the components.

As shown in FIG. 4, distillation column 410 provides unit operation 405a includes, where a mixer 428 couples the distillation column 410 to a reactor 430 performing unit operation 405b, and to a fractionator 450 performing unit operation 405c. Flow streams or fixed process stream connections 406 in chemical process facility 402 include feedstock 412, product 1 414, distillation column output 460, recycle 462, mixer output 464, reactor output 466 and product 2 468.

The operation of the chemical process facility 402 is simulated using calculation management system 400. Calculation management system 400 includes a process simulation computer 490 including a processor 495 that is coupled to a storage device such as memory 492, a user interface 498 and a display 496. Memory 492 stores process modeling software 494. Process modeling software 494 when executed by the process simulation computer 490 can perform any one or more of the methods, processes, operations, applications, or methodologies described herein. The process modeling software 494 includes a disclosed simulation algorithm described above that determines a default calculation order for the top-level DAG as well as a default calculation order within each SCCG.

The process simulation computer 490 executing process modeling software 494 can interact with a user via user interface 498 and display 496 with a GUI for interacting with the user. The process simulator represents each of the unit operations 405a, b, c on the display 496 with several user selectable unit operation options (operation options) that each have their own stored specification parameters.

EXAMPLES

Figure 5:
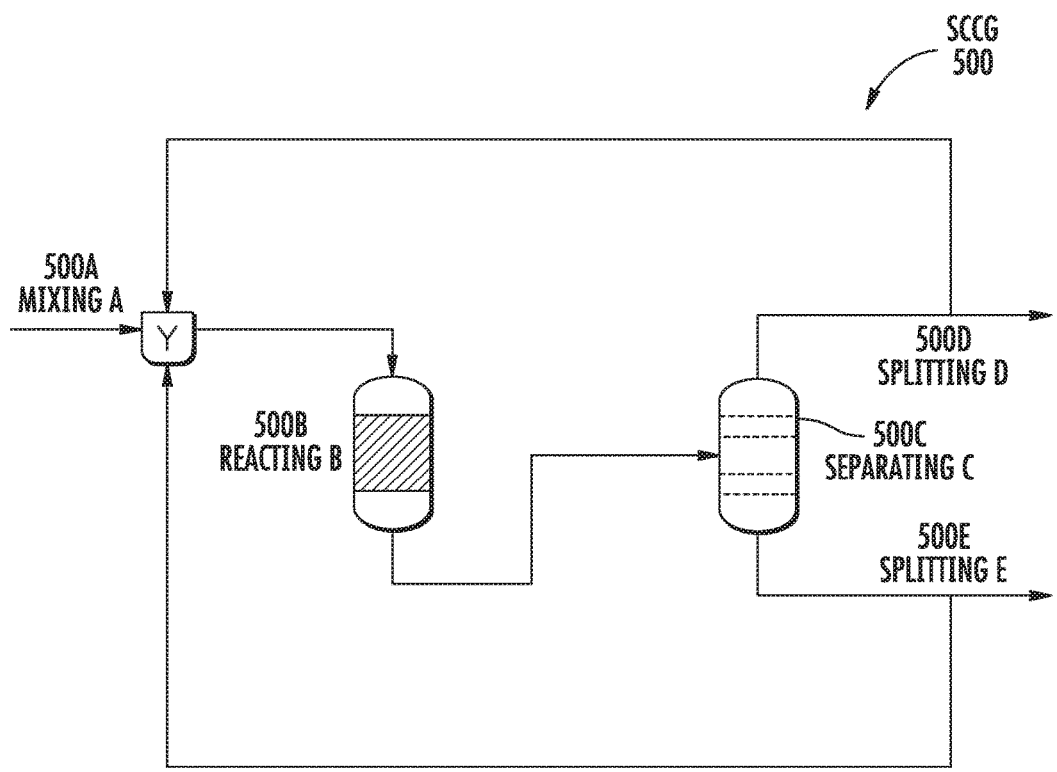
FIG. 5 is an example portion of a simple flowsheet with two recycle streams contained within a SCCG.

FIG. 5 illustrates an example portion of a simple flowsheet with two recycle streams contained within a SCCG 500. What is shown in FIG. 5 corresponds to step 106 described above ("graphically displaying said SCCGs and said components as nodes and said process streams as edges with a graphical indication representing each said cycle for the SCCGs, along with said initial calculation order, wherein the initial calculation order is user modifiable"), being here the graphical depiction of a single SCCG 500. In FIG. 5 the interconnected components shown which each perform chemical process unit operations are mixer 500A performing mixing operation A, reactor 500B performing reacting operation B, separator 500C performing separating operation C, splitter 500D performing splitting operation D, and splitter 500E performing operation E. There two recycle loops shown as section 2-500B-section 3-500C-section 4-500D-section 6-500A, and section 2-500B-section 3-500C-section 5-500E-section 7-500A. These two loops share a common section being section 2-500B-section 3-500C. It is noted although FIG. 5 does not explicitly indicate the cycles, nor the location of the tear stream(s)

where the recycle initialization is located, this information is also provided in the step 106 graphical display of the SCCGs.

The SM process simulator with calculation management system 400 provides the user information about the location of the recycle loops within the SCCG visually as shown in FIG. 5, textually or both, and the tear stream locations can be specified or modified by the user. The SM process simulator with calculation management system 400 can optionally suggest a tear stream location.

For this example, the user can select a single tear stream at one of the common sections (section 2 or section 3), or a separate tear stream for each recycle loop (section 4/5, and section 6/7). Once the tear streams are located in the SCCG 500, a default calculation is determined and a recycle convergence method is specified. For example if section 2 is the user selected tear stream location, then the unit operations can be solved in an order reacting B-separating C-splitting D-separating E-mixing A, whereas if section 3 is the section used, the selected tear stream location the operations can be solved in the order splitting C-separating D-separating E-mixing A-and reacting B.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

As will be appreciated by one skilled in the art, the subject matter disclosed herein may be embodied as a system, method or computer program product. Accordingly, this Disclosure can take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, this Disclosure may take the form of a computer program product embodied in any tangible medium of expression having computer usable program code embodied in the medium.

The invention claimed is:

1. A method of chemical process simulation, comprising:
providing a Sequential-Modular process simulator comprising a computing system including a processor having an associated memory along with a stored simulation algorithm, said algorithm implementing said method, comprising:
responsive to receiving a process flowsheet, creating a directed graph (DG) which represents a topology of said process flowsheet that has a plurality of components that are interconnected which each perform chemical process unit operations as nodes and process streams including recycle streams represented as cycles, with dependencies between said process streams adding additional said cycles to said DG;
partitioning said plurality of components in said DG into a first portion comprising strongly-connected component groups (SCCGs) that along with a remaining second portion comprises individual ones of said components;
providing an initial location for each of said cycles for said SCCGs to generate a directed acyclic graph (DAG);
determining an initial calculation order for said process flowsheet from said DAG, including an order for calculation within said SCCGs themselves, and
graphically displaying said SCCGs and said components as nodes and said process streams as edges with a graphical indication representing each said cycle for said SCCGs, along with said initial calculation order, wherein the initial calculation order is user modifiable.

2. The method of claim 1, wherein said algorithm further provides accommodation for accepting a user specified initialization and calculation method for said cycles.

3. The method of claim 2, wherein said user specified initialization and calculation method for said cycles comprises user specified initial estimates for at least one stream in each said cycles to allow said process flowsheet to solve, wherein updates of said initial estimates are made at each iteration of said calculation method, and wherein convergence of said chemical process simulation is achieved when said initial estimates and calculated results from said chemical process simulation agree within a user-specified tolerance.

4. The method of claim 1, wherein said determining said initial calculation order comprises topologically sorting said DAG.

5. The method of claim 1, further comprising before said determining said initial calculation order automatically providing said initial location for each of said cycles as a list of suggested locations and a number of independent ones of said cycles.

6. The method of claim 5, further comprising offering a user option to accept said initial locations or to specify other locations for said cycles.

7. The method of claim 6, further comprising offering a user an option to partition said cycles into sets of said cycles that are solved simultaneously and allowing specification of parameters of convergence algorithms.

8. The method of claim 1, wherein said partitioning is determined using Kosaraju's algorithm or Tarjan's strongly-connected components algorithm.

9. A Sequential-Modular (SM) process simulator, comprising:
a computing system including a processor having an associated memory along with a stored simulation algorithm, said algorithm implementing a method of chemical process simulation including calculation order management, said method comprising:
responsive to receiving a process flowsheet, creating a directed graph (DG) which represents a topology of said process flowsheet that has a plurality of components that are interconnected which each perform chemical process unit operations as nodes and process streams including recycle streams represented as cycles, with dependencies between said process streams adding additional said cycles to said DG;
partitioning said plurality of components in said DG into a first portion comprising strongly-connected component groups (SCCGs) that along with a remaining second portion comprises individual ones of said components;
providing an initial location for each of said cycles for said SCCGs to generate a directed acyclic graph (DAG);

determining an initial calculation order for said process flowsheet from said DAG, including an order for calculation within said SCCGs themselves, and graphically displaying said SCCGs and said components as nodes and said process streams as edges with a graphical indication representing each said cycle for said SCCGs, along with said initial calculation order, wherein said initial calculation order is user modifiable.

10. The SM process simulator of claim 9, wherein said algorithm further provides accommodation for accepting a user specified initialization and calculation method for said cycles.

11. The SM process simulator of claim 9, wherein said wherein said determining said initial calculation order comprises topologically sorting said DAG.

12. The SM process simulator of claim 9, further comprising before said determining said initial calculation order automatically providing said initial location for each of said cycles as a list of suggested locations and a number of independent ones of said cycles.

13. The SM process simulator of claim 12, further comprising offering a user option to accept said initial locations or to specify other locations for said cycles.

14. The SM process simulator of claim 9, further comprising offering a user an option to partition said cycles into sets of said cycles that are solved simultaneously and allowing specification of parameters of a convergence algorithms.

15. The SM process simulator of claim 9, wherein said partitioning is determined using Kosaraju's algorithm or Tarjan's strongly-connected components algorithm.

* * * * *